United States Patent
Lee et al.

(10) Patent No.: US 9,036,144 B2
(45) Date of Patent: May 19, 2015

(54) NANO-/MICRO-DROPLETS FOR THE DETECTION OF ANALYTES

(75) Inventors: Seung Joon Lee, Santa Barbara, CA (US); Brian D. Piorek, Santa Barbara, CA (US); Carl D. Meinhart, Santa Barbara, CA (US)

(73) Assignee: OndaVia, Inc., Hayward, CA (US)

( * ) Notice: Subject to any disclaimer, the term of this patent is extended or adjusted under 35 U.S.C. 154(b) by 110 days.

(21) Appl. No.: 13/289,679

(22) Filed: Nov. 4, 2011

(65) Prior Publication Data

US 2012/0281210 A1 Nov. 8, 2012

Related U.S. Application Data

(60) Provisional application No. 61/410,801, filed on Nov. 5, 2010.

(51) Int. Cl.
*G01N 21/65* (2006.01)

(52) U.S. Cl.
CPC .................... *G01N 21/658* (2013.01)

(58) Field of Classification Search
CPC .................... G01N 21/658; G01N 2021/8585; G01N 2021/8578
USPC .................... 356/300–301, 432, 436
See application file for complete search history.

(56) References Cited

U.S. PATENT DOCUMENTS

| | | | | |
|---|---|---|---|---|
| 6,180,415 | B1 * | 1/2001 | Schultz et al. | 436/518 |
| 7,212,284 | B2 * | 5/2007 | Deng et al | 356/301 |
| 7,399,961 | B2 * | 7/2008 | Chen et al. | 250/288 |
| 7,570,355 | B2 * | 8/2009 | Kamins et al. | 356/301 |
| 7,576,854 | B2 * | 8/2009 | Wang et al. | 356/301 |
| 7,651,863 | B2 * | 1/2010 | Hulteen et al. | 436/165 |
| 8,213,004 | B2 * | 7/2012 | Naya et al. | 356/301 |
| 2006/0249672 | A1 * | 11/2006 | Grimm et al. | 250/288 |
| 2006/0275541 | A1 * | 12/2006 | Weimer | 427/96.1 |
| 2008/0074662 | A1 * | 3/2008 | Gu et al. | 356/301 |
| 2010/0144059 | A1 * | 6/2010 | Frisk et al. | 436/518 |
| 2011/0267608 | A1 * | 11/2011 | Ou et al. | 356/301 |

OTHER PUBLICATIONS

Guoqing Wang, "Surface-enhanced Raman scattering in nanoliter droplets towards high-sensitivity detection of mercury (II) ions" May 15, 2009.*
Paper of M. Becker, "The SERS and TERS Effects Obtained by Gold Droplets on Top of Si Nanowires" Dec. 4, 2006.*

* cited by examiner

*Primary Examiner* — Kara E Geisel
*Assistant Examiner* — M. S.
(74) *Attorney, Agent, or Firm* — NUPAT, LLC; Morrison Ulman

(57) ABSTRACT

For a rapid and real-time SERS detection of organic chemicals in the air and the interfaces of air/solids, colloidal silver and/or gold nanoparticles solution is sprayed, in the form of nano-/micro-sized droplets, at the desired target area where the analytes of interest are present, e.g., in the air or onto certain organic/inorganic interfaces.

5 Claims, 2 Drawing Sheets

NANO-/MICRO-DROPLETS FOR THE DETECTION OF ANALYTES

CROSS-REFERENCE

This application claims the benefit of U.S. Provisional Application No. 61/410,801, filed Nov. 5, 2010, which application is incorporated herein by reference in its entirety.

FIELD OF INVENTION

The invention relates to detecting chemical species in the gas phase or particulates. The particulates may be airborne or deposited on a targeted surface. More particularly, the invention relates to detection and/or analysis of low concentration chemical species using nano- and/or micro-droplets comprising a surface enhanced Raman spectroscopy (SERS)-active nanostructure(s).

BACKGROUND

Low concentrations of chemical species (analytes) targeted for detection and analysis pose unique technical challenges. Because low-concentration detection and analysis of some chemical compounds necessitate large and heavy lab apparatus, field deployment is often rendered difficult or impossible. In addition, the targeted analytes may be hazardous (e.g., toxic, explosive, or the like).

There is a need for apparatus and processes that are both field portable and which offer accurate and repeatable detection/analysis of the targeted analyte(s). Applications include chemical detectors (e.g., hand-held chemical detectors or automated chemical detectors) for low-concentration analytes such as drugs, explosives, chemical and/or biological agents and weapons used in terrorist activities, and biological metabolites.

SUMMARY OF INVENTION

The invention provides systems and processes suitable for analyzing and/or detecting analytes (e.g., airborne particulates, gas phase, or surface deposited particulates). Various aspects of the invention described herein may be applied to any of the particular applications set forth below or for other types of SERS-based analyte detection devices and systems. The invention may be applied as a stand-alone system or method, or as part of an integrated solution, such as a portable analyte detection system. It shall be understood that different aspects of the invention can be appreciated individually, collectively, or in combination with each other.

In some embodiments, systems or devices described herein include hand-held chemical detectors for low-concentration analytes, such as those derived from drugs, explosives, and biological systems, which are operable from a safe distance.

In some embodiments, provided herein is an analyte detection system suitable for the detection of analytes, the system comprising:

a. nano- or micro-droplets comprising SERS-active material or ions thereof and a fluid; and
b. a Raman spectrometer configured to allow interrogation of the SERS-active surface of the SERS-active material (e.g., nanostructures comprising a SERS-active surface) or an analyte adsorbed thereon.

In certain embodiments, provided herein is an analyte detection system suitable for the detection of low volatility molecules, the system comprising:

a. a plurality of nano- or micro-droplets comprising SERS-active material or ions thereof and a fluid;
b. a device for deploying the droplets to a location to be analyzed; and
c. a Raman spectrometer to allow interrogation of the SERS-active surface of the SERS-active material (e.g., nanostructures comprising a SERS-active surface) or an analyte adsorbed thereon.

In some embodiments, provided herein is process for detecting analytes (e.g., low volatility and/or low concentration analytes) in a target area, the process comprising:

a. deploying a plurality of nano- and/or micro-droplets to the target area, the nano- and/or micro-droplets comprising SERS-active material or cations thereof and a fluid;
b. optionally reducing SERS-active material cations to SERS-active material;
c. optionally collecting the SERS-active material (which may or may not have analyte adsorbed or otherwise deposited thereon); and
d. interrogating with a Raman spectrometer the SERS-active material or analyte deposited thereon.

In some embodiments, any analyte detection system described herein further comprises a device for collecting the droplets (which may remain in discrete form or may have combined during collection) or SERS-active material or ions thereof from a deployed location. In certain embodiments, the collected droplets and/or SERS-active material (which may comprise analyte adsorbed thereon) are collected in a SERS interrogation region, e.g., a chamber comprising a SERS inert surface, e.g., glass. In some embodiments, the collection device is a vacuum or a swab. In certain embodiments wherein the collection device is a swab, the swab may comprise a glass wool swab which can be interrogated. In some embodiments, the analytes are low-volatility molecules. In certain embodiments, the analytes are in the form of particulates (e.g., airborne and/or deposited on a surface), and/or vapor (i.e., in the gas phase).

In some embodiments, the Raman spectrometer is integrated with telescopic optics for remote interrogation and analysis of the SERS-active materials and/or analyte. In certain embodiments, the droplet is deployed to a remote location in a manner so as to allow an amount of SERS-active material (or the analytes adsorbed thereon) to be interrogated by the Raman spectrometer integrated with telescopic optics.

In certain instances, the fluid is or comprises an inert and/or aerosolizable liquid. In some embodiments, the fluid is or comprises alcohol, water, or the like. In certain instances, varying the liquid is useful for tuning the Raman interrogation results. For example, depending on the analyte targeted, different liquids may be utilized (e.g., to potentially solubilize the analyte and condense with the analyte on the SERS-active surface). In some embodiments, different liquid carriers include, by way of non-limiting example, polar liquids, polar aprotic liquids, high-volatility liquids, low-volatility liquids, hydrophobic liquids, hydrophilic liquids, or the like. In specific embodiments, suitable liquids comprise alcohol, water, or the like. In specific embodiments, the liquid is inert (e.g., substantially inert, particularly to the analyte being targeted). In some embodiments, depending on the analyte targeted, different fluids may be utilized (e.g., to potentially solubilize the analyte and condense with the analyte on the SERS-active surface).

In certain embodiments, the device for deploying the droplets to a target area may be any suitable device, e.g., an aerosol. In some embodiments, an aerosol device utilized a propellant to deploy the droplets to the target area (i.e., the area of interest wherein analytes to be tested are or are potentially present). Propellants useful herein include any suitable propellant including, e.g., compressed air, nitrogen, argon, chlorofluorocarbons, hydrocarbons, carbon dioxide, nitrous oxide, fluorocarbons, lower alkyl ethers, such as dimethyl ether or methyl ethyl ether, or the like.

In some embodiments, the SERS-active materials (e.g., nanostructures comprising SERS-active materials) comprise noble metals (e.g., nanostructured metallic power(s), including, e.g., nanoparticles), nanostructured granule(s) of SERS active materials (e.g., noble metallic granule(s), such as, nanoparticles or microparticles), nanostructured inorganic beads or other structures whose surfaces are coated with a SERS-active material or substrate (e.g., noble metallic nanoparticle(s) or nanostructure(s) or layers), inorganic beads (e.g., microstructured beads) whose surfaces are coated with a SERS-active material or substrate (e.g., noble metallic nanoparticle(s) or nanostructure(s) or layers), and any other suitable substrate(s).

In certain embodiments, the Raman spectrometer comprises an interrogation laser and Raman sensor. The Raman sensor detects and measures vibrational signatures resulting from interrogation of SERS-active materials, or analytes deposited thereon. In certain embodiments, the laser is a collimated laser. In some embodiments, the Raman spectrometer is integrated with large-aperture telescopic optics. In certain embodiments, the Raman spectrometer is integrated with small-aperture telescopic optics.

In some embodiments, systems or devices described herein comprise one or more reservoir composition comprising SERS-active material or ions thereof, fluid, and an optional propellant. In certain instances, droplets are produced from the reservoir composition at various times (e.g., over periodic intervals) and deployed to the target location. In further or alternative embodiments, a system or device described herein may comprise a plurality single-use compositions comprising SERS-active material or ions thereof, fluid, and an optional propellant. In certain instances, nano- and/or microdroplets are produced from different single-use compositions at various times (e.g., over periodic intervals) and deployed to the target location. In certain embodiments, such systems are multiple use systems and/or are long-term monitoring systems. In some embodiments, such multiple use or long-term monitoring systems comprise an automated configuration to incrementally deploy a SERS-active material, or ions thereof, to a desired location and sample the air at the desired location. In certain instances, the automated configuration is a timer system, a system based on a triggering mechanism (e.g., opening a shipping container door within which the automated system is situated), or the like. In further or alternative embodiments, the multiple use and/or long-term monitoring system comprises a configuration to allow manual sampling of the air. Manual configurations may be independently or in combination with automated configurations.

In some embodiments, chemicals (e.g., unknown analytes or specifically targeted analytes) which are present in the air or deposited on a surface are adsorbed or otherwise deposited on the SERS-active material. In certain embodiments, droplets described herein comprise a liquid which evaporates upon deployment and facilitates deposition of the analyte on the SERS-active material.

In certain embodiments, a droplet described herein comprises an ion of a SERS-active material. In specific embodiments, the ion of the SERS-active material is a cation which is reduced to neutral form utilizing a reducing agent. In some instances, use of ions of SERS-active materials instead of or in addition to SERS-active materials in the droplets may facilitate deployment of the SERS-active materials and/or facilitate deployment of increased concentrations/amounts.

Applications include chemical detectors for low-concentration analytes (such as those derived from drugs, explosives, environmental monitoring, toxin monitoring, contaminant monitoring, reaction reagent or product monitoring, and biological systems) and capable of both short-term, manually operated analysis, and long-term, automated monitoring and analysis.

In some embodiments, the analyte detection system further comprises at least one module configured to chemometrically process at least one output of the analyte detection system. In further or alternative embodiments, the system further comprises at least one module configured to adjust one or more variable operating parameters of the system (e.g., use of different fluids, use of different SERS-active materials, use of ions of SERS-active materials, concentration of SERS-active materials and/or ions thereof in a droplet, number of droplets, length of interrogation, location of interrogation, or the like). In specific embodiments, at least one module is configured to adjust one or more variable operating parameters of the system is configured to adjust the one or more variable operating parameters based on the results of the chemometric processing of at least one output of the system.

As analytes interact with and/or are adsorbed or otherwise deposited onto SERS-active materials, they can be detected and/or analyzed using a variety of technologies. For example, the analytes may be studied using methods such as surface enhanced vibrational spectroscopy, surface plasmon resonance spectroscopy, electrochemical analysis techniques, molecular recognition elements, fluorescent chemical marker techniques, fluorescence quenching, redox-labeled nucleic acid binding techniques (including, but not limited to, the molecules DNA, RNA and PNA), X-Ray absorption techniques, IR, visible, UV, and other electromagnetic radiation absorption and spectroscopic techniques, mass spectroscopy techniques, liquid chromatography techniques, flame ionization analysis techniques, DNA melting point techniques, or titration analysis techniques.

BRIEF DESCRIPTION OF THE DRAWINGS

The foregoing features and other aspects of the invention are explained in the following description taken in conjunction with the accompanying figures. Further understanding of the features and advantages of the invention will be obtained by reference to the following detailed description that sets forth illustrative embodiments, in which the principles of the invention are utilized.

DETAILED DESCRIPTION OF INVENTION

Figure 1:
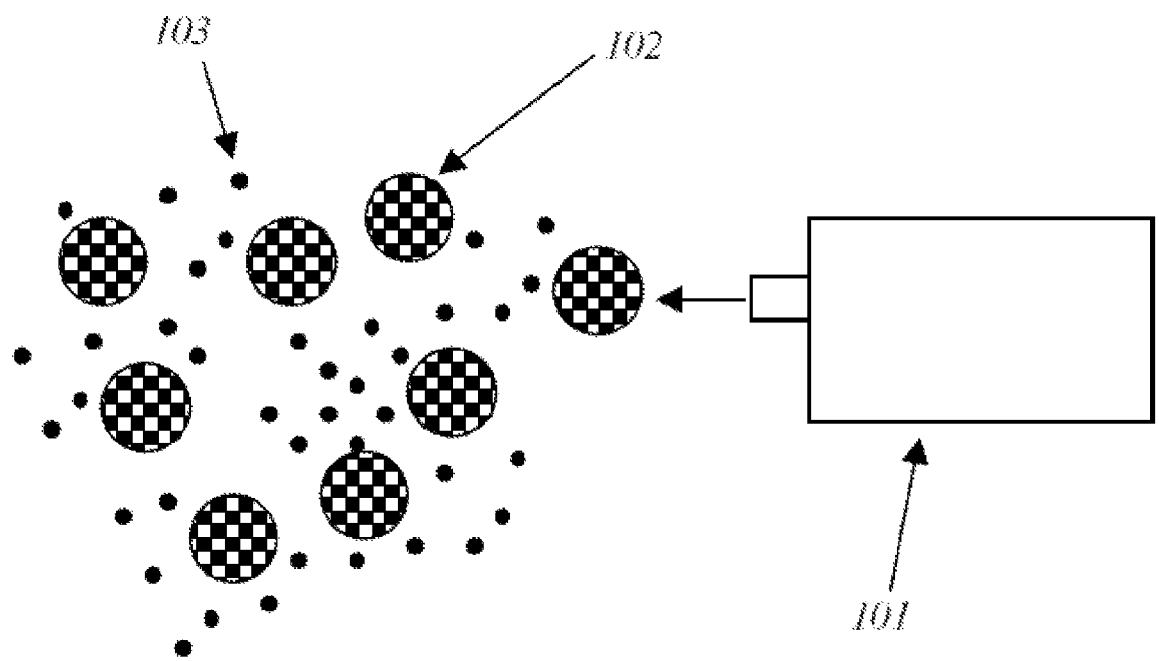
FIG. 1 illustrates a system useful for detecting airborne or gas phase analytes according to one embodiment described herein.
Figure 2:
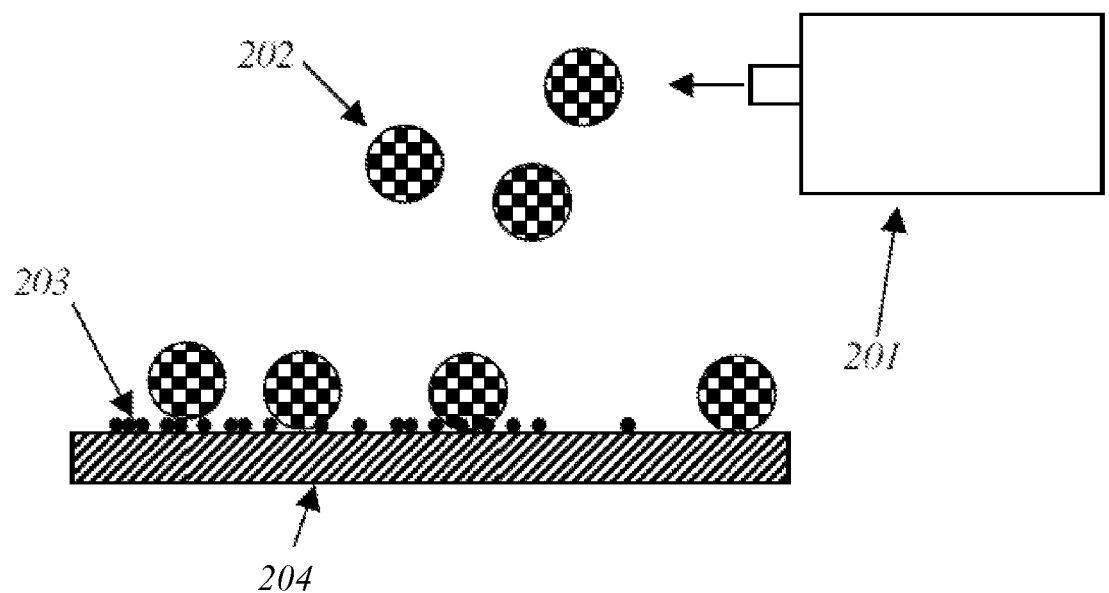
FIG. 2 illustrates a system useful for detecting analytes on the surface of a substance according to one embodiment described herein.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The foregoing features and other aspects of the invention are explained in the following description taken in conjunction with the accompanying figures, wherein:

Development of reproducible, renewable (refreshable), and cost-effective SERS-active substrate(s) has been of growing interest for SERS monitoring of chemical and biological species. Currently available SERS substrates, however, do not readily accommodate field requirements, which often make the use of SERS in chemical and biological detection applications troublesome.

In certain embodiments herein, we describe a versatile SERS platform that utilizes dynamic nano-/micro-droplets of colloidal nanoparticles for rapid and real-time SERS detection of organic chemicals, including gas-phase analytes and solid-phase dried analytes (which are often present on the surfaces of certain materials, e.g., interfaces of organics(analytes)/inorganics(metal, semiconductors, etc).

In certain embodiments, a colloidal solution (or colloid) is sprayed, in the form of nano-/micro-sized droplets (e.g., about 100 nm to about 100 μm in diameter), at a desired target area where the analytes of interest are or may be present, e.g., into the air or onto certain organic/inorganic interfaces. In certain instances, the notably small volume (e.g., a nano- or pico-liter or less) of colloidal nano-/micro-droplets provide extremely high surface-to-volume ratio that allows an effective accumulation of trace-levels of analytes into the colloidal matrix through diffusion and/or dissolution processes, thus enabling a rapid aggregation of nanoparticles therein (when appropriately mixed with concentrated analytes) by adsorbate-induced colloidal aggregation (necessary for a SERS enhancement). In some instances, because each droplet (with an appropriate control of droplet size) contains a limited (or known) number of nanoparticles (as compared to the bulk colloidal solution that is commonly applied for SERS measurement), over-aggregation-driven decreases and/or disappearance of SERS activity—which is often a major drawback in conventional colloidal SERS—is minimized.

In certain embodiments, real-time SERS interrogation of the analyte-admixed colloidal nano-/micro-droplets at one or more specified wavelengths provides molecule-specific vibrational fingerprints of organic chemicals.

Applications include chemical detectors for low-concentration analytes present in the air and/or onto certain interfaces. The detection and investigation of hazardous materials and explosives under field conditions presents multiple challenges: 1) how to conduct detection and analysis without hazarding human investigators; and, 2) how to conduct detection and analysis rapidly and accurately. Because certain applications—such as rapid deployments into and across threat zones—do not readily allow the use of robots and/or sophisticated approach methods due to time constraints, it is desirable that a system be rapidly deployable, which allows for operation from a safe distance.

Applications of the present invention include but are not limited to chemical detectors for low-concentration analytes—such as those derived from drugs, explosives, and biological systems—that are capable of both short-term and long-term analysis, which may be manual or automated.

FIG. 1 illustrates one embodiment of a system according to the present invention. FIG. 1 illustrates a nano-/micro-droplet generator (101), colloidal SERS-active material (e.g., silver and/or gold) nanoparticles in the form of nano-/micro-droplets (102); and the presence of analytes in the air (103). In certain embodiments, a SERS-active material is sprayed, in the form of nano-/micro-sized droplets, at a target area, e.g., ambient air, where the analytes of interested are present or may be present. In some embodiments, the droplets comprise colloidal SERS-active material (e.g., colloidal silver and/or gold nanoparticles). The nano-/micro-droplets (e.g., colloidal nano- and/or micro-droplets) are generated using any suitable method (e.g., electrospray, pulsed jet, or any other methods that can generate fine colloidal aerosols).

FIG. 2 illustrates one embodiment of the present invention wherein a SERS-active material (e.g., colloidal silver and/or gold nano-/micro-droplets) is sprayed, in the form of nano-/micro-sized droplets, on a target surface. FIG. 2 illustrates a nano-/micro-droplet generator (201), colloidal SERS-active material (e.g., silver and/or gold) nanoparticles in the form of nano-/micro-droplets (202), and analytes (203) present on the surface of certain substances (204). In certain embodiments, the organic analytes of interest are on the target surface (e.g., physisorbed or chemisorbed thereon). In certain embodiments, such surface-situated analytes are diffused and/or dissolved into the colloidal nano-/micro-droplets, thereby creating SERS-active aggregates with analytes. In various embodiments, SERS interrogation is performed either by direct exposure of specific areas on the interface(s) or by collecting such aggregates. In specific embodiments, collection of the aggregates is achieved through swabbing with appropriate substances such as inert glass wool or any other suitable mechanism, such as vacuum, paper-based materials, or textile-based materials.

In certain embodiments, any droplet (i.e., nano- or micro-droplet) described herein is present in a suitable size. In some embodiments, the size of the droplet is a size having a surface-to-volume ratio suitable for (1) facilitating an effective accumulation/concentration of trace-levels of analytes into a SERS-material matrix through diffusion and/or dissolution; and/or, (2) facilitate rapid aggregation of nanoparticles in a controlled way (e.g., by adsorbate-induced colloid). In some embodiments, the droplet diameter has a size of about 10 nm to about 500 microns. In certain embodiments, the droplet diameter is about 50 nm to about 250 microns. In specific embodiments, the droplet diameter is about 100 nm to about 100 microns. In various embodiments, systems described herein utilize a plurality of droplets for delivery to a target area. In some embodiments, at least 50% of the droplets of any system described herein have a diameter of about 50 nm to about 250 microns. In certain embodiments, at least 70% of the droplets of any system described herein have a diameter of about 50 nm to about 250 microns. In some embodiments, at least 85% of the droplets of any system described herein have a diameter of about 50 nm to about 250 microns. In certain embodiments, at least 95% of the droplets of any system described herein have a diameter of about 50 nm to about 250 microns. In some embodiments, at least 50% of the droplets of any system described herein have a diameter of about 100 nm to about 100 microns. In certain embodiments, at least 70% of the droplets of any system described herein have a diameter of about 100 nm to about 100 microns. In some embodiments, at least 85% of the droplets of any system described herein have a diameter of about 100 nm to about 100 microns. In certain embodiments, at least 95% of the droplets of any system described herein have a diameter of about 100 nm to about 100 microns. In certain embodiments, a device utilized to deploy the droplets is utilized to control the size of the droplets.

Droplets described herein may have any suitable volume. In some embodiments, volumes may be on the scale of nano liter (e.g., 1-1000 nL), pico liter (e.g., 1-1000 pL), or less. In some embodiments, a droplet described herein comprises a plurality of SERS-material nanoparticles (e.g., colloidal nanoparticles). In specific embodiments, a droplet described herein comprises a limited (or known) number of nanoparticles (e.g., a small number, such as about 1 to about 500, about 1 to about 200, about 1 to about 100, about 2 to about 50, or the like). In some embodiments, the constitution of these droplets provides an extremely high surface-to-volume ratio that: (1) allows an effective accumulation/concentration of trace-levels of analytes into the colloidal matrix through diffusion and/or dissolution; and therefore, (2) enables a rapid aggregation of nanoparticles in a controlled way by adsorbate-induced colloid.

In certain instances, the small volumes of colloidal nano-/micro-droplets provide extremely high surface-to-volume ratios that allow an effective accumulation/condensation of trace-levels of gas-phase analytes into the colloidal matrix through diffusion and/or dissolution, thereby enabling a rapid aggregation of nanoparticles therein with concentrated analytes by adsorbate-induced colloidal aggregation. Since low-volume droplets contain a small number of nanoparticles (when droplet size is appropriately optimized), control of the nanoparticles' aggregation process is obtained, thus maximizing SERS activity by preventing over-aggregation of nanoparticles (large uncontrolled precipitates), a common source of noise in SERS detection.

In some embodiments, SERS-active materials described herein may undergo multiple cycles of aerosolization. In certain embodiments, the SERS-active materials may be deployed to a target zone in a first droplet, collected, and re-deployed in a second droplet. This process is optionally repeated as many times as desired until a sufficient quantity of analyte is collected in order to obtain a desired reading (e.g., a reproducible and/or reliable analysis of analytes in the target area). In other words, multiple cycles may be repeated in order to increase the exposure of the nanoparticles to analyte. In certain embodiments, the multiple cycles may be repeated until dry (i.e., all fluid has vaporized or otherwise been removed). In other embodiments, cycling of the SERS-active materials may include the use of additional amounts of fluid. In certain embodiments, the liquid may be refreshed periodically or continuously in order to maintain the substrate in a wet state.

In some embodiments, SERS interrogation is performed on a collection substrate or in a designed chamber/device capable of vacuum-driven collection of such aggregates onto a suitable substance. Suitable substances include, e.g., SERS inactive substances, SERS substances which can be baselined, Si wafers, or the like. Furthermore, remote SERS interrogation with stand-off Raman instrumentation may be implemented to gather SERS signals.

In one embodiment, instead of using as-prepared droplets comprising SERS-active materials (e.g., SERS-active nanoparticles, such as colloidal silver and/or gold nanoparticles), liquid solutions of ions of SERS-active materials (e.g., silver or gold ions) are used. In some embodiments, a droplet described herein that comprises ions of SERS-active materials further comprises one or more reduction agents, such as sodium citrate or sodium borohydride. In certain embodiments, a plurality of droplets comprising ions of SERS-active material and one or more reducing agent are directly sprayed at the target regions where analytes are present, e.g., into the ambient air or onto certain organics/solid interfaces. In some instances, the analytes of interest are accumulated as aforementioned; and the reducing agent is utilized to reduce the cations of SERS-active materials into SERS-active materials. For example, reduction of a SERS-active material may be performed with one or more specified laser wavelengths for SERS interrogation, the laser-driven photo/thermal-induced reduction of metal ions take place in real time, thereby aggregating the analyte-incorporated SERS-active silver and/or gold nanoparticles.

In one embodiment, swabbing is performed with appropriate substances such as inert glass wool to collect/accumulate any analytes that are present on surfaces, while intermittently spraying colloidal nano-/micro-droplets onto the swabber and interrogating said swabber for SERS signals.

In an alternative embodiment, air containing or suspected of containing analytes of interested is bubbled periodically or continuously through a small volume of colloidal silver and/or gold nanoparticle solution so as to force the accumulation/concentration of the analytes by virtue of the maximized contact surface area between the colloidal solution and air. The adsorbate (analyte)-induced nanoparticles' aggregates in the colloidal matrix can be interrogated by a Raman laser and optics for SERS detection and analysis of analytes.

In one embodiment, a porous material may also be utilized, for instance a silicate or zeolite. In certain embodiments, a droplet described herein may comprise the porous material. In other embodiments, a porous material may be utilized instead of a droplet. In other words, in some embodiments, a nano- or micro-particle comprises a porous material with a SERS-active material, or ions thereof, in the pores thereof. As with the processes described herein for deployment of droplets, these porous materials may be deployed to a target area in any suitable manner.

In some embodiments, use of a porous material is used to facilitate a suitable surface-to-volume ratio of SERS-active material (e.g., colloidal silver and/or gold nanoparticles). In certain embodiments, use of a porous material is used to facilitate a suitable surface-to-volume ratio of SERS-active material ions (e.g., liquid solution of silver and/or gold ions, optionally with reduction agents such as sodium citrate and sodium borohydride). In certain instances, such formulations facilitate effective accumulation/concentration of the analytes into a sufficiently small volume of substances and hence enhancing the nanoparticles' aggregation for SERS detection of analyte(s).

Any suitable porous material is optionally utilized in any system, device or process described herein. For example, porous silicas and/or zeolites are well-known for their controllable pore sizes, ranging from, e.g., about 20 to about 1000 nm. In addition, in certain instances, suspended nanoparticles of SERS-active materials interact with pore walls to form SERS hotspots within the porous material volume. This interaction can be enhanced with suitable surface chemistry, for instance by tethering nanoparticles to pore walls with thiolated silanes, etc. Once nanoparticles are contained within the porous volume, the porous material may be interrogated with a Raman laser. Said laser can penetrate into the semi-transparent porous material volume, especially in the case of silicates, to provide a Raman interrogation of a 3-dimensional volume existing within the material. Since resulting SERS intensity used for interrogation of analytes existing within the porous volume increases with total interrogated volume, the 3-dimensional interrogation improves, in some instances, signal-to-noise ratios for analyte detection and analysis.

In one embodiment, SERS-active materials (e.g., gold and/or silver) nanoparticles of varying sizes and chemical characteristics are drawn from reservoirs and combined with a controlled amount of water to form colloid. In certain embodiments, various nanoparticles may be utilized in response to a variation of a variable operating parameter of the system, e.g., as a result of a chemometric process. In some embodiments, the makeup of colloid may be changed in order to optimize or otherwise improve or tune the response of the system as a whole.

In some embodiments, any droplet, colloid, or SERS-active material (including, e.g., collected SERS-active materials that have been deployed and collected) is sprayed into the air and/or onto a substrate using ink jet technology. Such a substrate includes a surface in a target area or a surface in a region or chamber used in the system for SERS interrogation and analysis. In some embodiments, the substrate, SERS-active material deposited thereon (and/or analyte adsorbed on the SERS-active material) is interrogated with a Raman laser. In certain instances, additional SERS-active material may be sprayed onto a surface (or may continue to be deposited upon the surface upon settling from the air if droplets described herein are deployed into the air) and cumulatively add layers to the SERS-active materials on the surface. In certain instances, the increasing amount of SERS-active materials being deposited on the surface (e.g., spray that continues to add layers) may provide for an increase in Raman signal and/or reduce the signal to noise ratio thereof. In some instances, a surface (e.g., a surface in a SERS interrogation region or chamber) may become contaminated. In such an event, the substrate may be automatically or manually moved to hide the contaminated region and expose a new, fresh region. In such an embodiment the method of moving the substrate may be by any suitable mechanism, e.g., by rolling and unrolling a flexible substrate film.

What is claimed is:

1. A process for detecting airborne analytes comprising:
   (a) spraying a plurality of micro-droplets from a micro-droplet generator into a target volume of air, the micro-droplets comprising SERS-active nanoparticles, and the micro-droplet generator comprising an aerosol propellant;
   (b) after analytes in the target volume of air have adsorbed onto the SERS-active nanoparticles in the micro-droplets, collecting the micro-droplets on a substrate; and,
   (c) detecting via Raman spectroscopy the analytes adsorbed onto the SERS-active nanoparticles.

2. The process of claim 1 wherein the micro-droplets have a mean diameter of about 10 nm to about 500 microns.

3. The process of claim 1 wherein the nanoparticles comprise gold or silver.

4. The process of claim 1 wherein the aerosol propellant comprises compressed air, compressed nitrogen or chlorofluorocarbons.

5. The process of claim 1 further comprising: evaporating the micro-droplets after they are collected on the substrate, leaving the analytes adsorbed onto the SERS-active nanoparticles on the substrate.

\* \* \* \* \*